(12) United States Patent
Ryan et al.

(10) Patent No.: US 8,057,092 B2
(45) Date of Patent: Nov. 15, 2011

(54) DISPOSABLE SPINNER FLASK

(75) Inventors: John A. Ryan, Clinton, MA (US); Todd M. Upton, Eliot, ME (US); Kathy M. Youngbear, Cambridge, MA (US)

(73) Assignee: Corning Incorporated, Corning, NY (US)

( * ) Notice: Subject to any disclaimer, the term of this patent is extended or adjusted under 35 U.S.C. 154(b) by 449 days.

(21) Appl. No.: 11/986,931

(22) Filed: Nov. 27, 2007

(65) Prior Publication Data

US 2008/0131957 A1 Jun. 5, 2008

Related U.S. Application Data

(60) Provisional application No. 60/861,924, filed on Nov. 30, 2006.

(51) Int. Cl.
*B01F 13/08* (2006.01)
(52) U.S. Cl. ............ 366/274; 366/325.92; 435/302.1
(58) Field of Classification Search ........... 366/273, 366/274, 325.92, 329.1; 435/299.1, 302.1
See application file for complete search history.

(56) References Cited

U.S. PATENT DOCUMENTS

| | | | | |
|---|---|---|---|---|
| 195,803 A * | 10/1877 | Clous | | 68/57 |
| 2,958,517 A * | 11/1960 | De Long et al. | | 435/302.1 |
| 3,649,465 A * | 3/1972 | Scharf et al. | | 435/302.1 |
| 3,744,764 A * | 7/1973 | Sedam | | 366/274 |
| 3,888,466 A * | 6/1975 | Sedam | | 222/394 |
| 4,290,300 A * | 9/1981 | Carver | | 73/32 R |
| 4,355,906 A | 10/1982 | Ono | | 366/274 |
| 4,483,623 A * | 11/1984 | Eaton et al. | | 366/247 |
| 4,512,666 A * | 4/1985 | O'Connell | | 366/249 |
| 4,912,048 A * | 3/1990 | Smith et al. | | 435/299.2 |
| 4,993,841 A * | 2/1991 | Lofgren et al. | | 366/274 |
| 5,074,671 A * | 12/1991 | Roueche et al. | | 366/172.1 |
| 5,167,449 A | 12/1992 | Killough | | 366/247 |
| 5,183,336 A | 2/1993 | Poltorak et al. | | 366/273 |
| 5,267,791 A | 12/1993 | Christian et al. | | 366/249 |
| 5,407,270 A | 4/1995 | Barile et al. | | 366/247 |
| 5,798,261 A * | 8/1998 | Koontz | | 435/283.1 |
| 6,109,780 A | 8/2000 | Lesniak | | 366/253 |
| 6,244,741 B1 * | 6/2001 | Akamine et al. | | 366/325.92 |
| 6,536,938 B2 * | 3/2003 | Zhou | | 366/273 |
| 6,844,186 B2 | 1/2005 | Carll | | 435/289.1 |
| 6,991,933 B1 * | 1/2006 | Upton et al. | | 435/299.2 |

(Continued)

FOREIGN PATENT DOCUMENTS

GB 2178971 A * 2/1987

(Continued)

OTHER PUBLICATIONS http://www.nalgenelabware.com/products/productDetail.asp?product_id= 100&subcategory_id=140&category_id=140&brand_name=NALGENE+Labware&category_name=Culture+Vessels&subcategory_name=2007.

*Primary Examiner* — David Sorkin

(74) *Attorney, Agent, or Firm* — Susan S. Wilks; Thomas R. Beall

(57) ABSTRACT

The present invention relates generally to a cell culture stirring vessel and associated impeller. More particularly, it relates to a fully integrated, disposable spinner flask vessel having a suspended impeller assembly permanently integrated therein. The invention is particularly suitable for use in applications where cells are suspended within a liquid medium with minimal shear forces.

17 Claims, 5 Drawing Sheets

U.S. PATENT DOCUMENTS

2001/0043508 A1* 11/2001 Zhou .............................. 366/273
2003/0008389 A1* 1/2003 Carll ........................... 435/302.1
2003/0058736 A1* 3/2003 Nielsen .................... 366/325.92
2004/0062140 A1* 4/2004 Cadogan et al. .............. 366/144
2006/0194310 A1* 8/2006 Upton et al. ............... 435/299.1
2007/0053238 A1* 3/2007 Kocienski ..................... 366/273
2007/0253288 A1* 11/2007 Mennenga et al. ........... 366/274

FOREIGN PATENT DOCUMENTS

WO      WO 01/021760 A3 * 10/2002

* cited by examiner

DISPOSABLE SPINNER FLASK

CROSS-REFERENCE TO RELATED APPLICATIONS

This application claims the benefit of U.S. Provisional Application Ser. No. 60/861,924 filed on Nov. 30, 2006 and entitled "Disposable Spinner Flask" which is incorporated by reference herein.

FIELD OF THE INVENTION

The invention relates to a cell culture stirring vessel and impeller. More particularly, a fully integrated, disposable spinner flask vessel having a suspended impeller assembly is disclosed. The invention is particularly suitable for use in applications where cells are suspended within a liquid medium with minimal shear forces.

BACKGROUND OF THE INVENTION

In various scientific fields, it is useful to grow cells in a culture media (such as a liquid suspension) over an extended period of time. However, increasing cell numbers results in the depletion of nutrients in the culture medium. When the media is allowed to stagnate, cell growth is inhibited and the cells can die.

Accordingly, the cell culture suspension must be stirred in order to effectively grow cells. A spinner flask is a type of cell culture vessel that employs a suspended impeller driven by an external rotating magnet under the base of the spinner flask to maintain the cells in suspension. However, impellers impart hydrodynamic stress on growing cells that can damage cells or alter their morphology. Impellers are usually suspended in the cell culture media and are stirred via a direct coupling to an overhead motor, or through magnetic induction from a rotating magnet in the base of the support for the culture flask. If the impeller rotation or movement is too strong or the blades are too rigid or too long, the cells may be sheared by the force of the impeller or blades. Likewise, if the impeller rotation or movement is too weak or the blades are too short, the cells may not remain suspended.

Further, care must be taken not to contaminate the culture media. Spinner flasks have typically consisted of glass and metal reusable cell culture vessels comprising an amalgam of working parts each of which requires cleaning, sterilization (usually by autoclave) and proper storage between uses. Therefore, there is a need for an inexpensive, disposable, pre-sterilized, fully integrated cell culture vessel which provides gentle stirring to prevent shearing and keep cells suspended.

BRIEF DESCRIPTION OF THE INVENTION

A disposable, polymeric, integral, pre-sterilized vessel for culturing cells is provided. The vessel comprises an integral vessel body having a top surface, bottom surface and a substantially cylindrical sidewall, an impeller assembly having a plurality of planar blades, located within the vessel around a central axis, and a flexible shaft extending from the top surface. The present invention further provides an impeller assembly having two major blades and two minor blades arranged in an alternating fashion around a central axis, the major blades having an upper portion and a lower portion, the upper portion having a substantially triangular shape, the lower portion having a substantially rectangular shape, the minor blades having a substantially triangular shape whereby a major blade alternates with a minor blade around the central axis. The present invention further provides a magnetic stirring bar integrally molded within the impeller assembly to provide, in combination with a magnetic stir plate, a means for rotating the impeller assembly within the vessel. In combination with the impeller assembly, the invention further provides baffles capable of creating the turbulence necessary to effectively nurture cells in suspension. The present invention also provides for an impeller assembly having blades that, at their farthest most extension from the shaft, come into close proximity with the vessel walls.

DETAILED DESCRIPTION OF THE DRAWINGS

Figure 1:
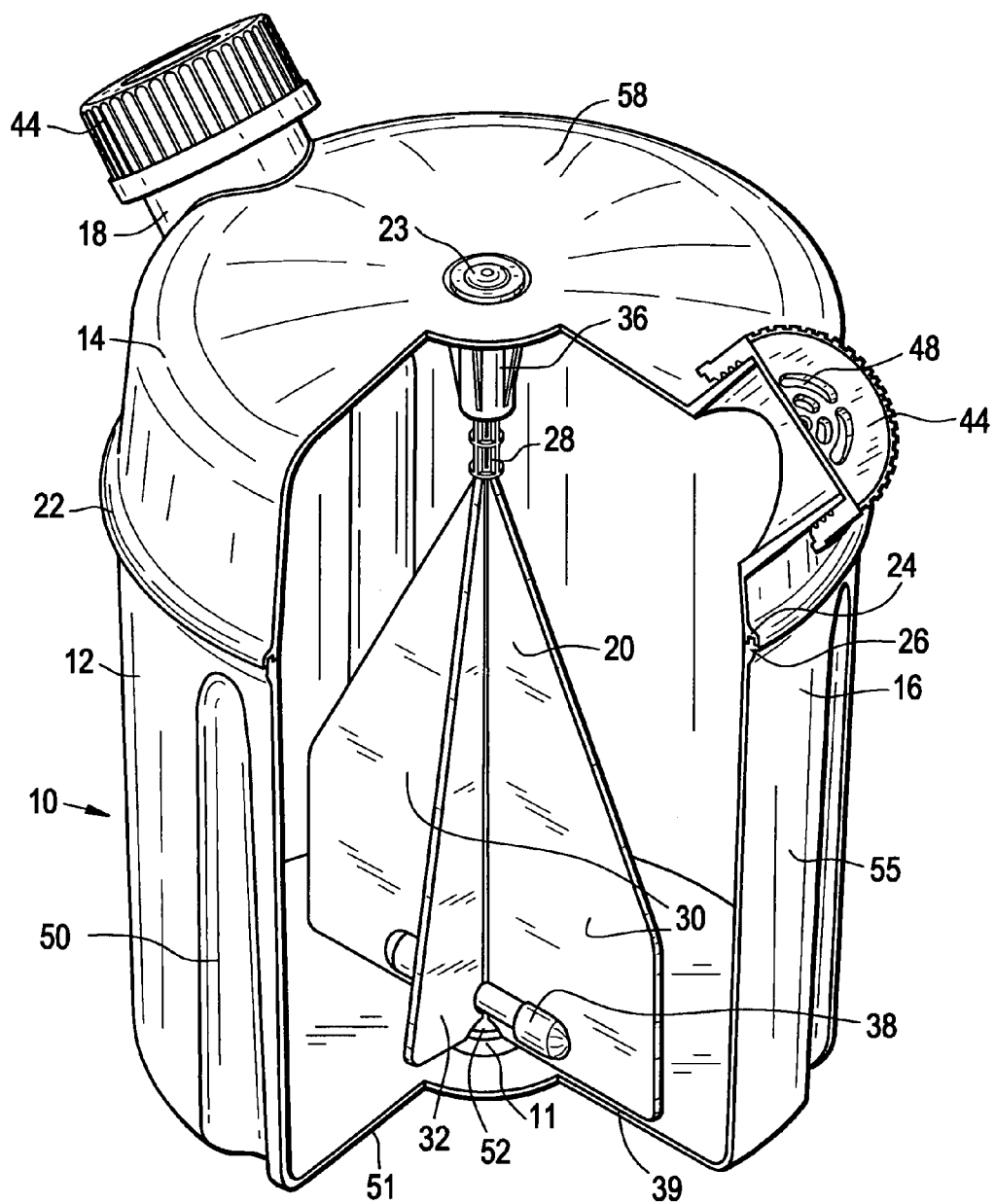
FIG. 1 is a cut-away perspective view of one embodiment of the stirring vessel of the present invention.
Figure 2:
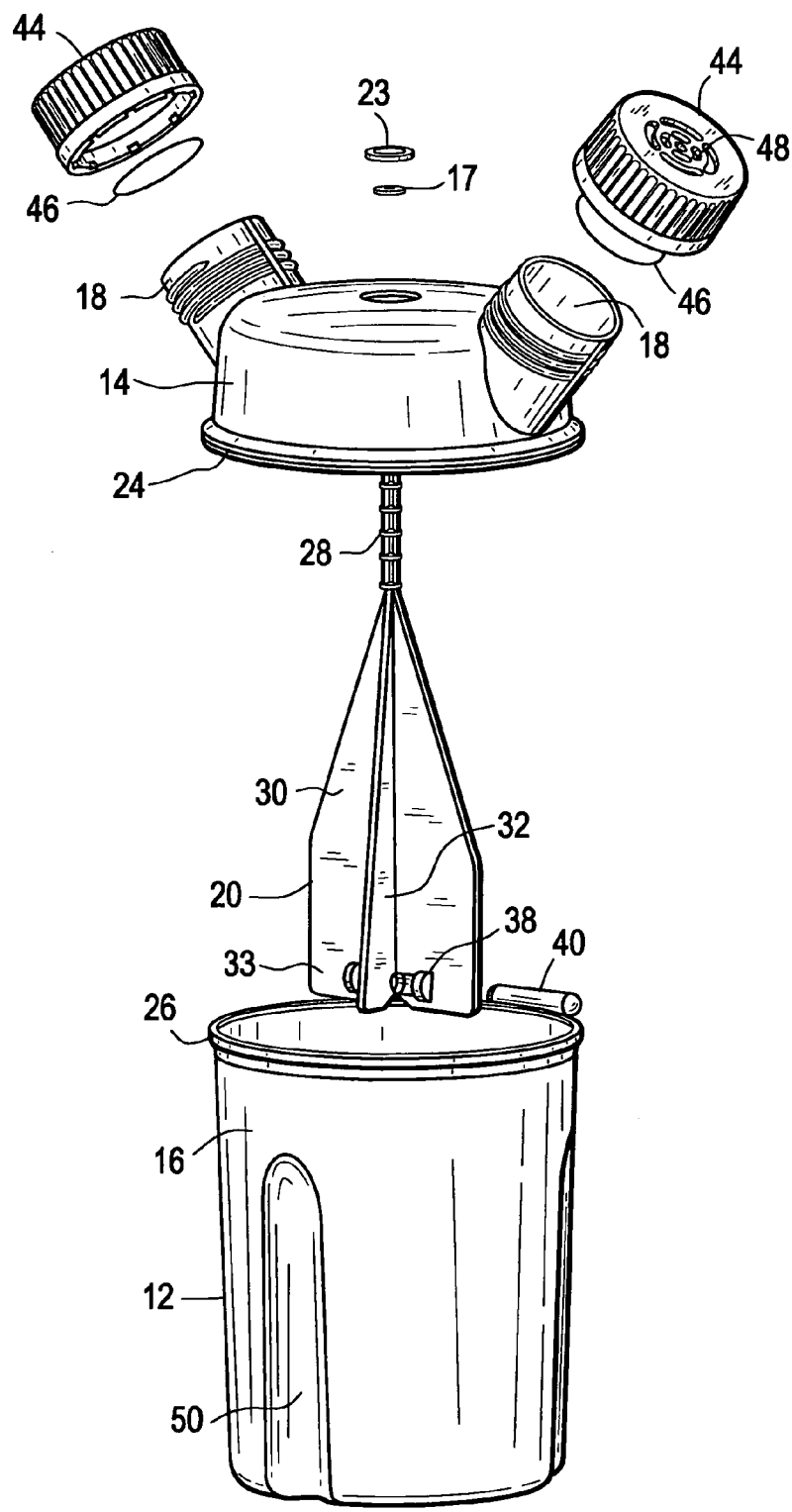
FIG. 2 is an exploded view of one embodiment of the stirring vessel of the present invention.
Figure 3:
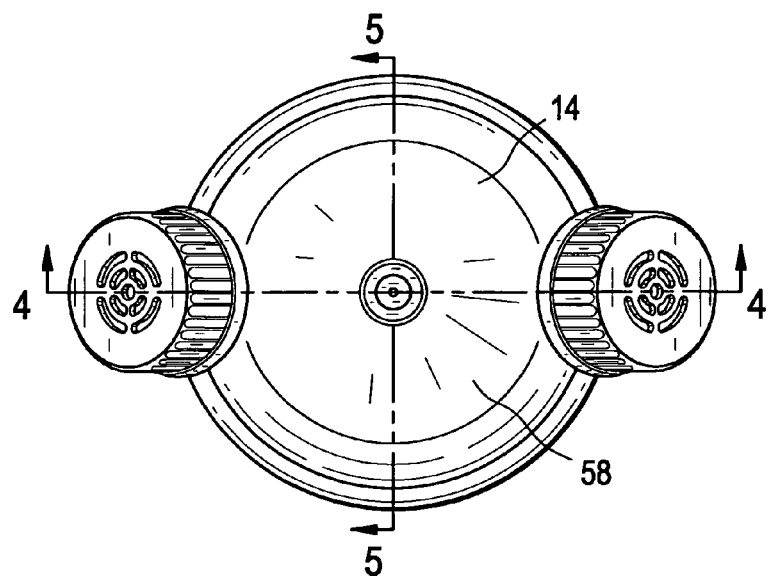
FIG. 3 is a top perspective view of one embodiment of the stirring vessel of the present invention.

Referring to FIGS. 1-7, a vessel 10 for cell culture is shown. The vessel comprises a vessel body 12 having a top portion 14 and bottom portion 16, necked access ports 18, and an impeller assembly 20. The top portion and bottom portion are circumferentially sealed along a weld line 22 which is the result of a joining of interconnecting lips 24, 26 circumscribing the periphery of both portions. The vessel 10 has a substantially cylindrical shape and a central axis $A$-$A_1$ with an inner surface, an outer surface, a top surface 58, sidewall 55 and a bottom surface 51 having a centralized raised hump 11. Although any size vessel is theoretically possible, the sizes for stirring vessels of the present invention typically range from 125 ml to 10 liters and specific sizes include 1 liter and 3 liter versions.

The impeller assembly 20 includes a flexible shaft 28 extending along the central axis. Extending from and contiguous with the shaft 28 are four paddle blades 30, 32 each disposed 90 degrees relative to each other. Of the four paddle blades 30, there are two major blades 30 and two minor blades 32. The major blades 30 are disposed 180 degrees relative to one another and likewise, the two minor blades are disposed 180 degrees relative to each another. The arrangement of blades around the central shaft creates an alternating effect of minor-major blade orientation. It is believed that this orientation provides enhanced mixing of fluid in both the lateral as well as vertical planes within the vessel. The blades represent planes that are oriented vertically when the vessel is sitting upright. It should be understood that other blade configurations, shapes and arrangements are possible, including those that employ fewer or more than four blades.

Figure 6:
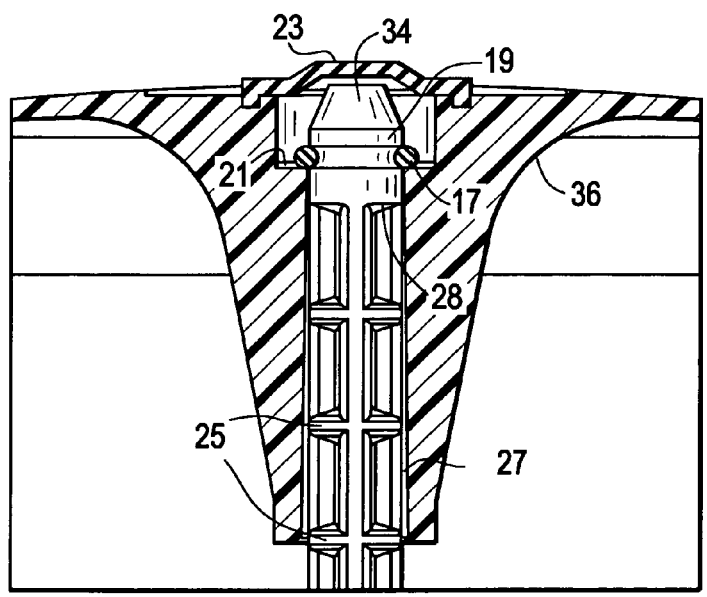
FIG. 6 is an enlarged view of the circled region identified in FIG. 4.
Figure 7:
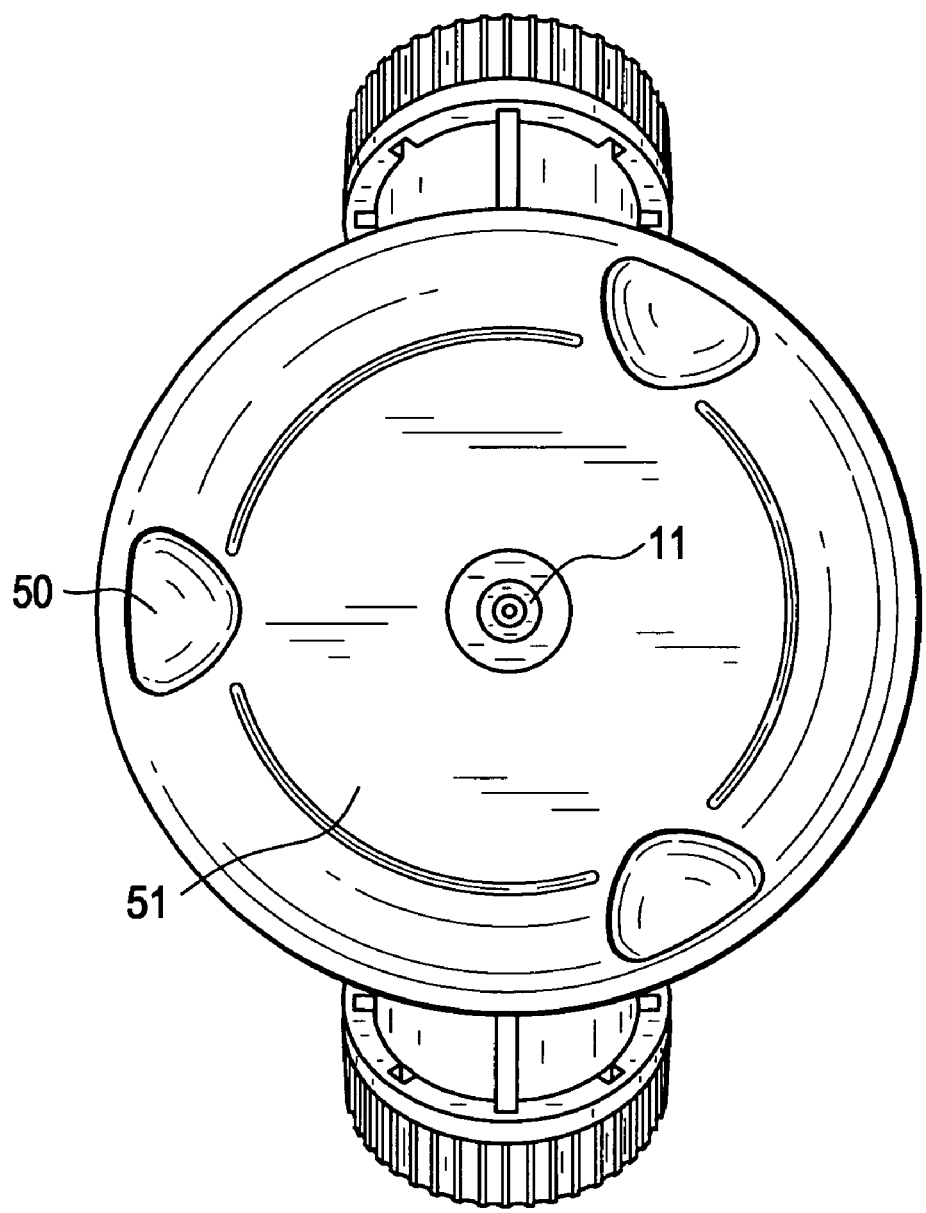
FIG. 7 is a bottom perspective view of one embodiment of the stirring vessel of the present invention.

Referring specifically to FIG. 6, the flexible shaft 28 has a substantially tapered top end 34 that is mounted in the top portion 14 of the vessel by contact with a shaft receptacle 36 centrally located and integral with the top surface of the top portion of the vessel. An o-ring 17 is located upon a receiving groove 19 on the shaft 28. The o-ring may be made from PTFE, nylon or other similar low-friction material. The o-ring rests against a circular shelf 21 in such a way that the impeller assembly hangs freely within the vessel. By having this single mounting point in the shaft receptacle, the flexible shaft 28 is free to rotate. A disc top 23 in the top surface 58 seals the shaft receptacle from the external environment. The flexible shaft 28 further advantageously has horizontal support ribs 25 that enhance the stiffness of the shaft. The shaft receptacle 36 has sidewalls that extend into the vessel creating a sleeve 27 for the shaft. The sleeve 27 maintains the shaft's orientation within the central axis and prevents any lateral movement of the impeller assembly 20 within the vessel.

The impeller assembly 20 has a substantially concave bottom end 52 shaped within the intersection of the bottom edges 39 of the respective blades. The concave section 52 substantially follows the contour of the raised hump 11, but is not intended to contact the hump when the vessel is positioned in an upright position. In fact, in this embodiment, there are no contact points between the impeller 20 and vessel below the shaft receptacle 36. This is advantageous in that it helps reduce the possibility of cell damage due to sheer. The hump feature 11 on the bottom surface 51 eliminates any potential dead spot directly below the central axis $A-A_1$ of the impeller assembly 20. The concave section 52 within the intersection point of the blades allows the blade edges 39 to come into close proximity with the bottom surface 51. In one embodiment, the distance between the blade and the bottom surface is between 0.05 inches and 0.5 inches. Since the vessel is intended to be shipped as an integral unit, the concave section 52 in combination with the raised hump 11 also serve to contain the impeller 20 during shipping in such a way that the impeller and associated magnet cannot damage the vessel walls through contact caused by jostling of the vessel.

Figure 4:
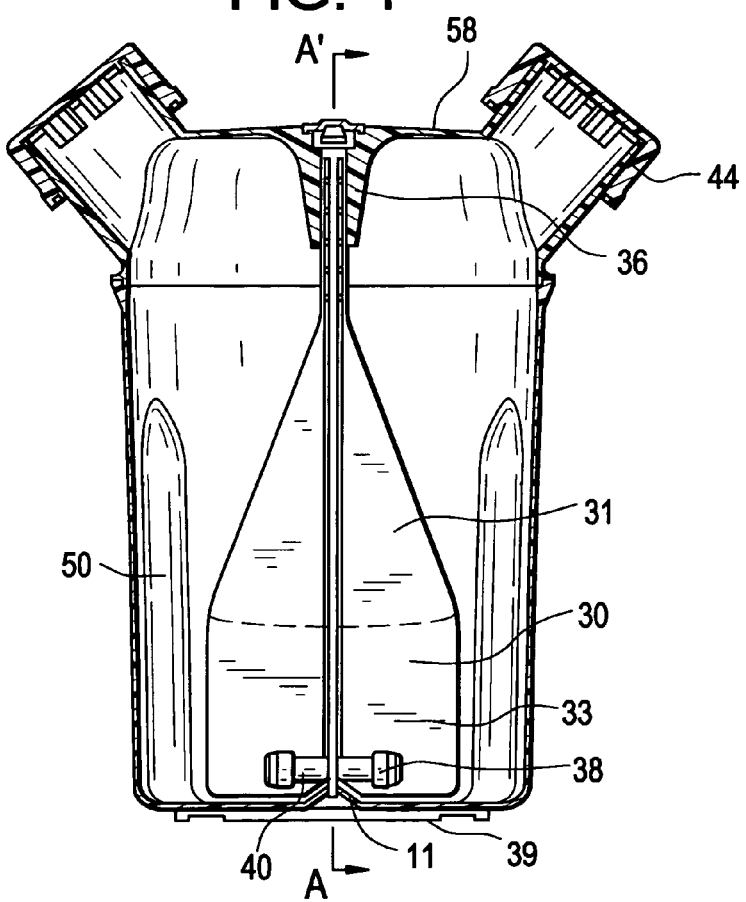
FIG. 4 is a cross section taken along line 4-4 of FIG. 3.
Figure 5:
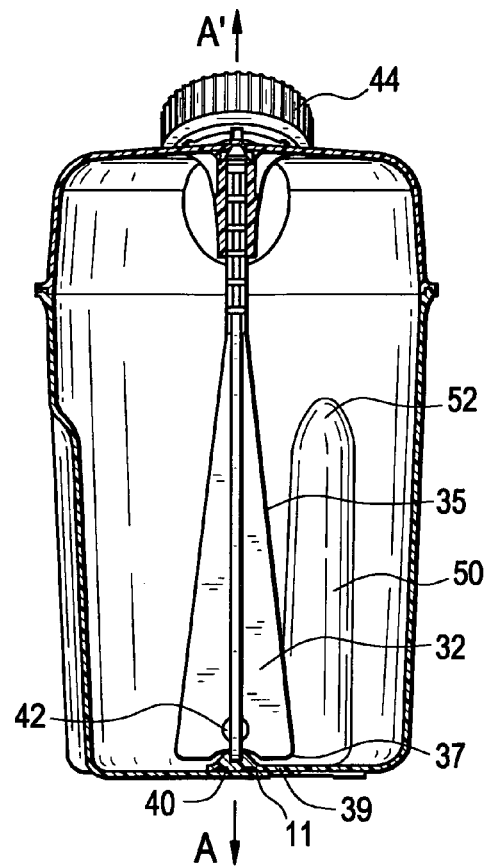
FIG. 5 is a cross section taken along line 5-5 of FIG. 3.

Referring specifically to FIG. 4 which is a vertical cross section of the vessel of one embodiment, each major blade 30 includes an upper portion 31 and a lower portion 33. The upper portion 31 has a substantially triangular shape with an outer edge progressively angled away from the shaft and central axis $A-A_1$. The lower portion 33 of each major blade 30 is substantially rectangular in shape. Referring specifically to FIG. 5 which is a cross section of the vessel taken 90 degrees from the section represented by FIG. 4, the minor blades 32 form a triangular shape along their entire length. The outer edge 35 of each minor blade 32 extends linearly away from the central axis $A-A_1$ to a point 37 at the blade's bottom edge. The bottom edges 39 of the lower portion of all blades 30, 32 (minor and major) extend generally parallel to the bottom surface 51 of the vessel, but do not contact the bottom surface. The impeller assembly including blades may be made from polypropylene, TPE, a silicone, or other appropriate polymeric materials.

A magnet receptacle 38 for receiving a magnetic stir bar 40 is molded into each lower portion 33 of the two major blades 30. A hole 42 in the minor blades 32 and shaft area completes the magnet receptacle 38. A cylindrical plug or magnetic stir bar 40 is mounted in the magnet receptacle 38 along the lower edge of the two major blades 30 and orthogonal to the minor blades 32. Alternatively, the magnet itself is molded into the impeller assembly 20. To accomplish this, a magnet is inserted into a mold and the impeller assembly is over-molded around the magnet itself. Having the magnet integrally molded within the impeller assembly provides the advantage that during assembly and shipping, the magnet cannot detach from the impeller assembly and damage the vessel body.

Access ports 18 extend outward from the top portion 14 of the vessel. Optional internally threaded sealing caps 44 are installed on exteriorly threaded ports 18. In one embodiment, the cap 44 has within it a hydrophobic membrane insert 46 made from material that will allow gas transport into the vessel interior but prevent liquid from escaping the vessel and other contaminants from entering the vessel. Examples of such membrane material include polytetrafluoroethylene and polyvinylidenefluoride (PVDF). In one embodiment, the caps further have a vent 48 that allows the necessary gaseous communication with the external environment. In another embodiment, accessories such as tubes may be employed and connected to the access ports to allow aseptic dispensing.

In one embodiment, the access ports 18 extend at an angle from horizontal to allow instruments such as pipettes to pass by impeller assembly 20 and reach adjacent regions of stirring vessels having preselected depths. Nevertheless, the dimensions of the access ports and the angles in which the access ports extend from the vessel body may be selected to optimize instrument accessibility to regions within various vessels. Further, although two access ports are disclosed in the figures, it will be appreciated that any number of ports are possible.

Baffles 50 extend along the interior wall in a vertical direction which is parallel to the central axis $A-A_1$. Each baffle 50 has roughly the cross-sectional shape of a half-cylinder or an isosceles triangle. Each baffle originates from the vessel bottom and extends vertically upward terminating in an elliptical shape 52. It is believed that having baffles extend completely through the liquid region (i.e. from the bottom surface 51 to a point above the liquid surface) enhances turbulence throughout the entire liquid domain. The baffles 50 project into the vessel cavity and, in combination with the impeller assembly 20, create and enable turbulence with the vessel interior. The baffles 50 are preferably formed integrally with the wall of the container. In one embodiment, there are three baffles 50 disposed symmetrically along the interior wall about the central axis, but the number and density of baffles may vary based on vessel size.

In one embodiment, the vessel of the present invention is made from injection molded polymer, for example polystyrene, polycarbonate or any other appropriate polymer as identified by one of skill in the art. In one embodiment, the polymer is optically transparent and non-cytotoxic. Since the materials are made from lightweight polymers and the vessel is pre-sterilized during manufacture, the vessel itself is disposable and there is no need for the end user to sterilize components of the system prior to use.

In one embodiment, the vessel sidewalls, top or bottom have openings that are sealed with gas permeable liquid impermeable films or membranes. In embodiments where these membrane of film covered openings are located in an area of the vessel that will contact the cell suspension, improved gas exchange with the external environment is achieved. As such, in one embodiment, the openings are located in the lower half of the sidewall 55 or in the bottom surface 51.

In describing the manufacturing and assembly process, the impeller assembly 20, top portion 14 and bottom portion 16 of the vessel body are molded separately and treated as discussed. Thereafter, the magnet 40 is placed in the magnet receptacle 38. As previously noted, in another embodiment, the magnet itself is over-molded and therefore integral with the impeller assembly. The impeller assembly 20 is placed within the shaft receptacle 36 of the top portion 14. The o-ring 17 is slipped over the top end of the shaft and contacted with the receiving groove 19. The top portion 14 and bottom portion 16 of the vessel are then permanently affixed to one another by, for example, ultrasonic welding along weld line 22 thereby creating a completely and permanently integral unit. Similarly, disc top 23 is welded in position sealing the shaft receptacle 36. In other embodiments, the parts are laser welded or attached by means of adhesives. In embodiments having necked access ports and caps, the caps are put into place and the unit is effectively sealed for shipment. The integral unit may then be sterilized. As most cell culture procedures are carried out under aseptic conditions by practicing the so-called sterile technique, the pre-sterilization of the vessel provides the culture chamber to be maintained in a sterile, closed environment. It is advantageous to have the cell culture process carried out in a system where the culture chamber is functionally closed to the external environment, with the sterile integrity maintained from the time the device is manufactured until it has been disposed. One method of pre-sterilizing includes gamma irradiation. Other sterilization methods known to those skilled in the art including ethylene oxide or electron beam irradiation treatment could also be used.

Based on the manufacturing approach and since the weld line 22 exists in the sidewall region of the vessel, the impeller assembly may be sized such that the blades extend nearly the full diameter of the vessel. In one embodiment, the impeller blades extend in at least one point, approximately 50-95% of the vessel's radius, as measured from the central axis to the sidewall. In another embodiment, at least one blade extends 75-95% of the vessel's radius but due the design and manufacturing approach, may extend any distance.

To operate the system of the invention, liquid (such as a culture media including cells) is delivered through the access ports 18 of the container. The liquid is added until it reaches a fluid level which is preferably below the top edge of the blades 30, 32 and the top of the baffles 50 but above the lower portion 33 of the major blades 30.

Once the liquid is in the vessel, the vessel is placed upon a magnetic stirring device (not shown) and the stirring device causes the magnetic stir bar 40 to spin within the vessel. As a result, the impeller assembly 20 including shaft 28 and blades 30, 32 is also caused to rotate within the vessel. The rotation of the assembly causes the fluid to stir within the container. Alternatively, the impeller may be rotated by a motorized mechanism engaging the top of the shaft. The shape of the blades 30, 32 and the interaction with the baffles 50 causes the liquid to circulate from a position near the top of the fluid level to a position near the bottom of the fluid level. The hump 11 prevents material from accumulating at the center of the bottom surface. Since the upper portion 31 of the major blades 30 extend above the fluid level, the surface area of the liquid in the container is effectively increased and continually agitated, resulting in aeration of the liquid.

The apparatus is used to stir cells suspended in a culture media. The cells may also be attached to micro-carrier beads suspended in the culture medium. This mixing can be performed over a relatively long time (i.e., from several hours up to several months) but must not produce great stress to cells suspended in the liquid. The mixing must be effective such that the liquid cycles from the bottom of the apparatus to the surface, and back again. Typically, the cells are maintained at about 27° C.-37° C. and mixed at 5 to 300 rpm. Of course, these conditions can be varied depending on the particular cells or application. Cells or cellular materials may be harvested through the access ports by means of pipette, pouring or pumping.

Although detailed descriptions of preferred embodiments of the invention have been disclosed herein, it will be apparent to those skilled in the art that various modifications and dimensional changes can be made thereto without departing from the spirit and scope of the invention as set forth in the following claims:

What is claimed is:

1. A vessel for culturing cells comprising:
an integral vessel body having a top portion having a top surface, a bottom portion having a bottom surface and a substantially cylindrical sidewalk;
wherein the top portion and the bottom portion are permanently affixed to each other;
an impeller assembly inside the vessel body having a plurality of planar blades, a central axis, a flexible shaft extending from the top surface, a magnet receptacle formed within the plurality of planar blades and a magnet nested within the magnet receptacle;
wherein the plurality of planar blades extend orthogonally from the central axis when the shaft rotates around the central axis;
wherein said vessel body is a polymeric material.

2. The vessel of claim 1 wherein said vessel is sterile.

3. The vessel of claim 1 wherein the impeller assembly further comprises four planar blades attached to the flexible shaft, each blade disposed at 90 degrees relative to blades on each side of it.

4. The vessel of claim 3 further comprising two major blades and two minor blades, the major blades having an upper portion and a lower portion; the upper portion having a substantially triangular shape, the lower portion having a substantially rectangular shape; the minor blades having a substantially triangular shape whereby a major blade alternates with a minor blade around the central axis.

5. The vessel of claim 1 further comprising a plurality of baffles integral with the sidewalls originating at the bottom surface and extending vertically a predetermined distance up the sidewall.

6. The vessel of claim 5 wherein the baffles each terminate in an elliptical shape.

7. The vessel of claim 5 having 3 baffles spaced an equal distance from one another around a perimeter of the sidewall.

8. The vessel of claim 1 wherein the polymeric material is non-cytotoxic and optically transparent polystyrene or polycarbonate.

9. The vessel of claim 1 further comprising at least one access port.

10. The vessel of claim 9 wherein the access port is a threaded neck engaged with a threaded vented cap.

11. The vessel of claim 10 wherein the top portion comprises a cap having a hydrophilic membrane.

12. The vessel of claim 1 wherein said flexible shaft is mounted to the top surface by mating with a shaft receptacle integral with the top surface.

13. The vessel of claim 1 wherein the vessel body has a radius measured by the distance from the central axis to the sidewall and wherein at least one blade extends, in at least one point, approximately 50-95% of the vessel's radius.

14. The vessel of claim 1 wherein the vessel body has a radius measured by the distance from the central axis to the sidewall and wherein at least one blade extends, in at least one point, approximately 75-95% of the vessel's radius.

15. The vessel of claim 1 wherein the plurality of blades do not touch, but come within 0.05 and 0.5 inches of the bottom surface.

16. The vessel of claim 1 wherein the top surface, bottom surface, or cylindrical sidewall has at least one opening therein, said opening sealed with gas permeable liquid impermeable films or membrane.

17. The vessel of claim 1 wherein the impeller assembly is sealed inside the vessel body.

* * * * *